(12) United States Patent
Liu et al.

(10) Patent No.: US 9,018,196 B2
(45) Date of Patent: Apr. 28, 2015

(54) DEVELOPMENT OF A NEW FORMULATION OVERCOMING THYMUS ATROPHY WITH CONCOMITANTLY ENHANCEMENT OF ANTI-INFLAMMATORY EFFECT OF DEXAMETHASONE

(71) Applicant: Macau University of Science and Technology, Macau (CN)

(72) Inventors: Liang Liu, Macau (CN); Ting Li, Macau (CN); Fenggen Yan, Macau (CN)

(73) Assignee: Macau University of Science and Technology, Macau ( * ) Notice: Subject to any disclaimer, the term of this patent is extended or adjusted under 35 U.S.C. 154(b) by 0 days.

(21) Appl. No.: 14/251,664

(22) Filed: Apr. 14, 2014

(65) Prior Publication Data

US 2014/0315867 A1   Oct. 23, 2014

Related U.S. Application Data

(60) Provisional application No. 61/814,803, filed on Apr. 22, 2013.

(51) Int. Cl.
*A61K 31/353* (2006.01)
*A61K 31/573* (2006.01)

(52) U.S. Cl.
CPC ............. *A61K 31/353* (2013.01); *A61K 31/573* (2013.01)

(58) Field of Classification Search
CPC .......................... A61K 31/353; A61K 31/573
USPC .................................................. 514/171, 456
See application file for complete search history.

(56) References Cited

PUBLICATIONS

Sempowski G. D., Rhein M. E., "Measurement of mouse T cell receptor excision circles", Current Protocols Immunology, 2004, Chapter 10, Unit 10 31.
Wang B. et al., "CD4+ Th1 and CD8+ type 1 cytotoxic T cells both play a crucial role in the full development of contact hypersensitivity", the Journal of Immunology, 2000, p. 6783-6790, 165.
Lynch H. E., Sempowski G. D., "Molecular measurement of T cell receptor excision circles", Methods Mol Biol., 2013, p. 147-159, 979.

*Primary Examiner* — Raymond Henley, III
(74) *Attorney, Agent, or Firm* — Eagle IP Limited; Jacqueline C. Lui (57) ABSTRACT

This invention provides a method of preventing and/or treating thymus degeneration comprising administering an effective amount of dihydromyricetin to a subject in need thereof, in which the degeneration is induced by dexamethasone. In one embodiment, the thymus degeneration is induced during the course of treatment of inflammation by dexamethasone.

11 Claims, 15 Drawing Sheets

| Group | Dose | n | DTH Induced by DNFB | | | | | | | |
|---|---|---|---|---|---|---|---|---|---|---|
| | | | 24 h | | 48 h | | | 72 h | | |
| | | | ΔT ± S.E.M. | % I | ΔT ± S.E.M. | | % I | ΔT ± S.E.M. | | % I |
| Control | | 15 | -6.667±5.315** | | 4.000±4.957** | | | -7.333±3.712** | | |
| Model(DNFB) | | 15 | 184.0 ±7.976 | | 196.7±7.015 | | | 185.3±6.239 | | |
| DEX | 1.5625 µg/ear | 15 | 122.0±9.621** | 33.7 | 102.0 ± 7.509** | | 48.1 | 85.33± 6.681** | | 54.0 |
| DMY | 1.0 mg/ear | 15 | 126.0 ±7.976 ** | 31.5 | 112.0 ± 7.635** | | 43.1 | 110.0 ±7.559** | | 40.6 |
| DEX (1.5625 µg/ear) + DMY (1.0 mg/ear) | | 15 | 89.33 ± 9.282** | 51.5 | 78.67 ± 6.084** | | 60.0 | 64.67 ± 5.595** | | 65.1 |

| Group | Dose | n | Thymus weight(mg) ±S.E.M | % I | P value |
|---|---|---|---|---|---|
| Control | | 15 | 53.33±3.032 | | ** |
| Model(DNFB) | | 15 | 40.34±2.028 | | †† |
| DEX | 1.5625 µg/ear | 15 | 33.93±2.219 | 15.9 | †† |
| DMY | 1.0 mg/ear | 15 | 43.02±2.444 | -6.6 | † |
| DEX (1.5625 µg/ear) + DMY (1.0 mg/ear) | | 15 | 43.25±2.258 | -7.2 | † |

| Group | Dose | n | DTH induced by DNFB | | | | | |
|---|---|---|---|---|---|---|---|---|
| | | | 24 h | | 48 h | | 72 h | |
| | | | ΔT ± S.E.M. | %I | ΔT ± S.E.M. | %I | ΔT ± S.E.M. | %I |
| Control | | 10 | -3.000 ± 4.955 ** | | -3.000 ± 3.350 ** | | -5.000 ± 4.014 ** | |
| Model (DNFB) | | 11 | 200.9 ± 5.793 | | 186.4 ± 5.094 | | 189.1 ± 7.441 | |
| DEX (1.5625 μg/ear) + DMY (1.0 mg/ear) | | 10 | 140.0 ± 7.303 ** | 30 | 77.00 ± 10.55 ** | 59 | 80.00 ± 8.300 ** | 58 |
| DEX (0.78125 μg/ear) + DMY (0.5 mg/ear) | | 10 | 141.0 ± 12.41 ** | 30 | 116.0 ± 7.775 ** | 38 | 110.0 ± 9.545 ** | 42 |

| Group | Dose | n | Thymus weight(mg) ±S.E.M | P value |
|---|---|---|---|---|
| Control | | 10 | 60.25 ±3.695 | * |
| Model(DNFB) | | 11 | 46.59±2.385 | † |
| DEX (1.5625 µg/ear) + DMY (1.0 mg/ear) | | 10 | 45.89±3.917 | †† |
| DEX (0.78125 µg/ear) + DMY (0.5 mg/ear) | | 10 | 40.34±2.267 | †† |

DEVELOPMENT OF A NEW FORMULATION OVERCOMING THYMUS ATROPHY WITH CONCOMITANTLY ENHANCEMENT OF ANTI-INFLAMMATORY EFFECT OF DEXAMETHASONE

CROSS-REFERENCE TO RELATED APPLICATION

This application claims benefit under 35 U.S.C. §119(e) of U.S. Provisional Application having Ser. No. 61/814,803 filed 22 Apr. 2013, which is hereby incorporated by reference herein in its entirety.

FIELD OF INVENTION

This invention relates to a formulation for reducing thymus atrophy, in particular, during the course of treatment of inflammation by dexamethasone. This invention also relates to a formulation for enhancing the anti-inflammatory effect of dexamethasone.

BACKGROUND OF INVENTION

Dexamethasone is effective to treat autoimmune disease as well as organ transplantation, while the strong immune-suppressive effect of the type drug could result in thymus atrophy, which further induces poor response of the immune system to new stimuli and protection to against infection, as the thymus is a primary lymphoid organ, able to generate mature T cells that is mediated immune-response.

SUMMARY OF INVENTION

In the light of the foregoing background, it is an object of the present invention to develop a formulation which could reverse thymus degeneration with concomitantly enhancement of anti-inflammatory effect.

In the first aspect, the present invention relates to a method of preventing and/or treating thymus degeneration comprising administering an effective amount of dihydromyricetin to a subject in need thereof.

In one embodiment, the thymus degeneration is induced by dexamethasone. In another embodiment, the thymus degeneration is induced during the course of treatment of inflammation by dexamethasone. In another embodiment, dexamethasone exhibits a synergistic effect with dihydromyricetin in treating inflammation. In yet another embodiment, the dosage ratio of dexamethasone and dihydromyricetin is from 1 to 640.

In another aspect of this invention, the present invention relates to a method of treating inflammation comprising administering an effective amount of dexamethasone and dihydromyricetin to a subject in need thereof, the dexamethasone exhibits a synergistic effect with the dihydromyricetin in treating inflammation.

In one embodiment, the administration of dexamethasone and dihydromyricetin can prevent and/or treat thymus degeneration during the treatment to inflammation. In another embodiment, the thymus degeneration is induced by dexamethasone. In another embodiment, the dosage ratio of dexamethasone and dihydromyricetin is from 1 to 640.

In yet another aspect, the present invention provides a formulation comprising an effective amount of dexamethasone and dihydromyricetin for treating inflammation, the formulation can prevent and/or treat thymus degeneration induced during the treatment.

In one embodiment, the thymus degeneration is induced by dexamethasone. In another embodiment, the dosage ratio of dexamethasone and dihydromyricetin is from 1 to 640.

DETAILED DESCRIPTION OF THE PREFERRED EMBODIMENTS

To study the effect of enhancing therapeutic efficacy and reducing adverse effects of dexamethasone on the inflammatory diseases and thymus atrophy, a formulation is developed, which comprises dexamethasone (DEX) and dihydromyricetin (DMY), with a ratio of 1/640 in one embodiment. It has been shown that the formulation could significantly inhibit inflammation and simultaneously prevent thymus atrophy.

The reference cited throughout this application is identified in square bracket as "[xx]" with xx referring to the number of the corresponding reference on the list of "References".

EXAMPLE 1

Study on the effect of DEX, DMY and the formulation comprising DEX and DMY on anti-inflammatory effects.

1.1 Procedure—The Delay-Type Hypersensitivity Test (DTHT) in Mice

Figure 1A:
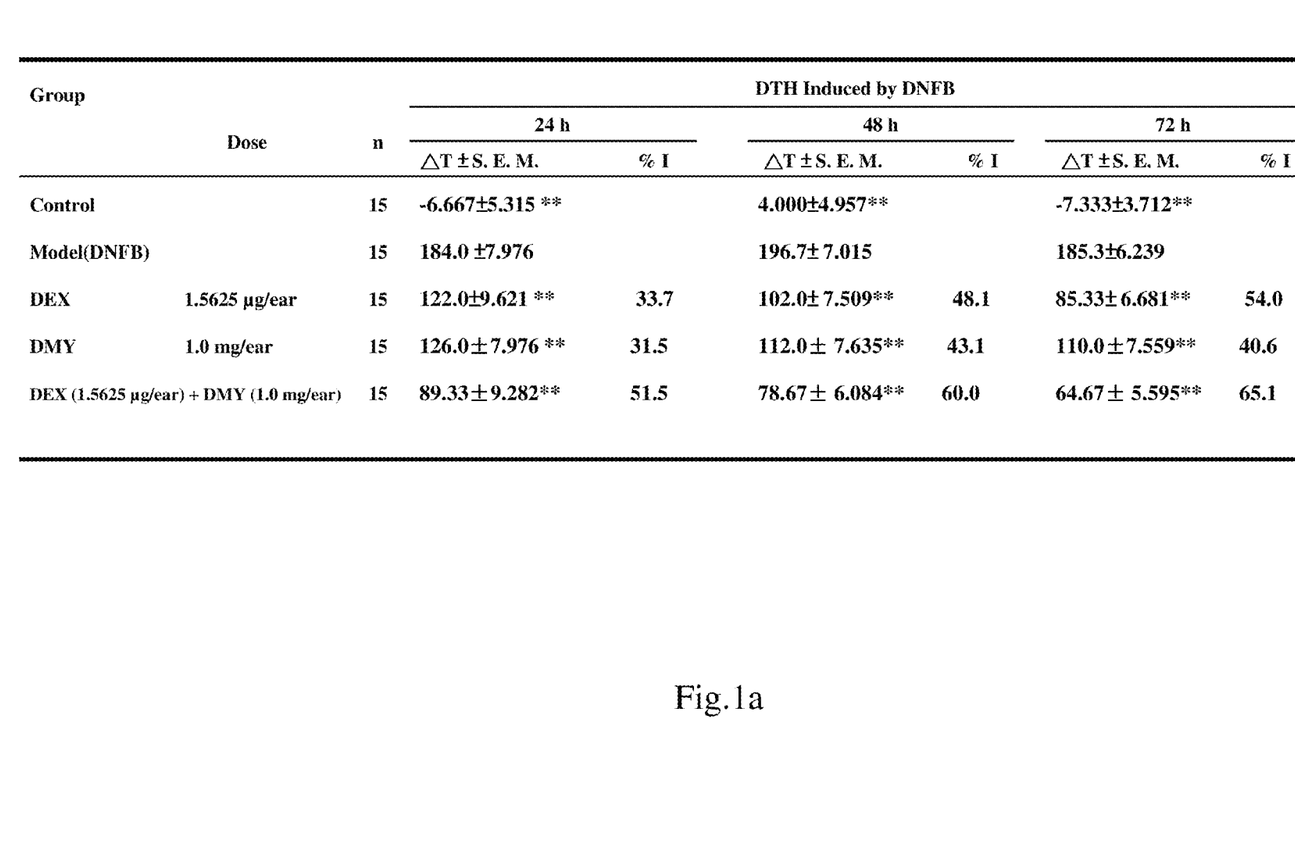
FIGS. 1a and b show the effect of different groups, including DEX, DMY and the formulation comprising DEX and DMY on ear edema of DTH mice induced by dinitrofluorobenzene (DNFB).

Male Balb/c mice, weighing 19-21 g were sensitized through topical application of 20 µl of 0.5% (v/v) DNFB in acetone onto the shaved abdomen on days 1 and 2. Challenge was then preformed on day 6 by applying DNFB (20 µl, 0.5%, v/v) on the left inner and outer ear surfaces of mice. DMY (at dosage of 1 mg/ear) and/or DEX (1.5625 µg/ml) dissolved in acetone was topically applied (20 µl) to the ears at $2^{nd}$, $24^{th}$, $48^{th}$, $72^{nd}$, hour after the challenge. The edema was calculated as the difference between the thickness of left and right ear at the $24^{th}$, $48^{th}$ and $72^{nd}$ h after challenge. FIG. 1a shows the average of the ear edema of the different groups of mice at that time spot. The control 100 group was treated only with DNFB or solvent solution.

1.2 Results

Figure 1B:
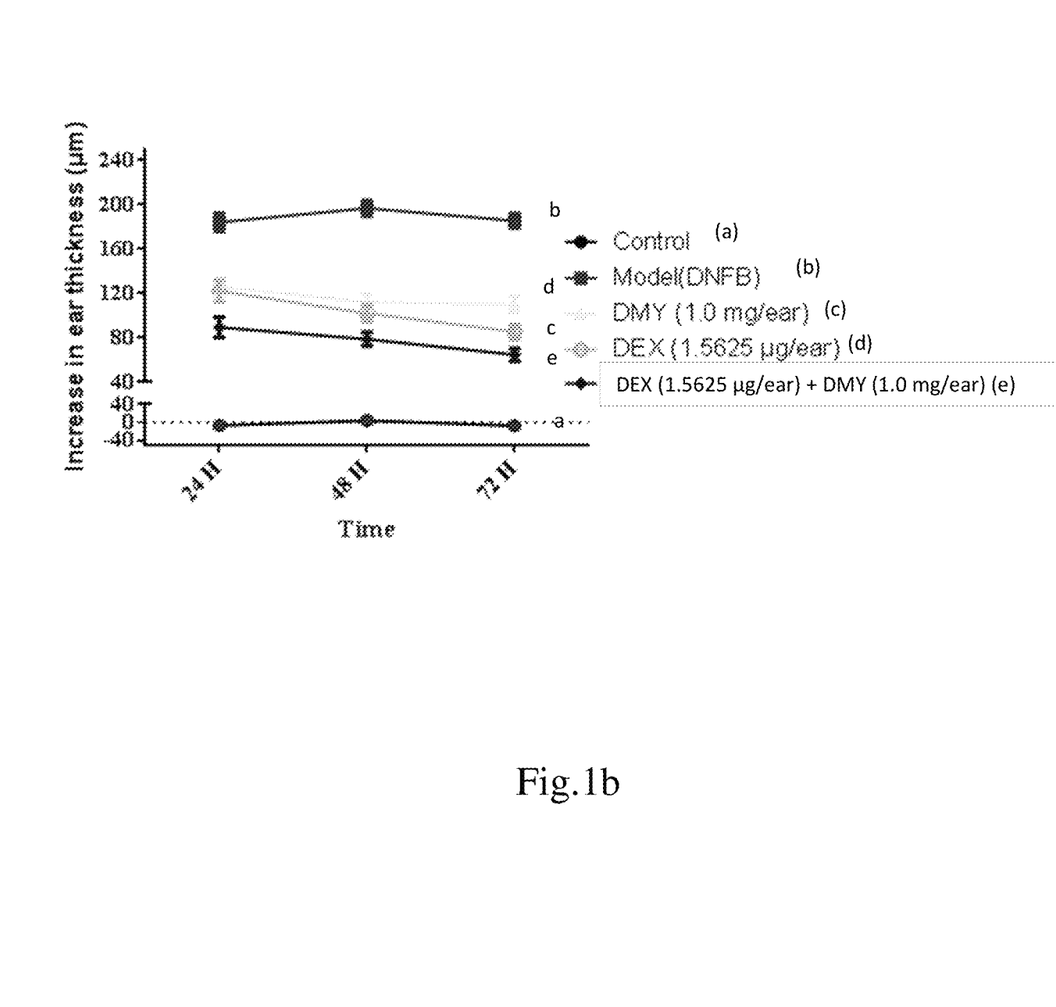

FIGS. 1a and 1b show the effects of DEX, DMY and the combinational application of DMY and DEX (illustrated as the DMY+DEX group) on treatment of ear edema of DTH mice induced by DNFB. Edema as expressed as the increase in ear thickness (ΔT in micrometer±S.E.M.) in the DNFB experiments. Percentages of inhibition (% I) for each measurement were calculated from values for the DEX, DMY and DMY+ DEX groups with respect to those for the Model Group. Statistically significant differences with respect to the Model Group are expressed as *$P<0.05$ and **$P<0.01$ (Dunnett's t test). It was shown that the percentages of inhibition of DMY+DEX group were significantly increased. Further, both DMY and DEX could inhibit ear edema of the mice, and the anti-inflammatory effect of DEX could be enhanced by DMY.

In short, Example 1 shows that the DMY could enhance the anti-inflammatory effect of DEX on ear edema of mice mediated by DNFB.

EXAMPLE 2

Study on the effect of DEX, DMY and the formulation comprising DEX and DMY on thymus atrophy.

2.1 Procedure and Results

The animal model was conducted as mentioned in section 1.1 of Example 1 above, in which after the mice were sacrificed by cervical dislocation, the spleens and thymuses were isolated and weighed.

Figure 2A:
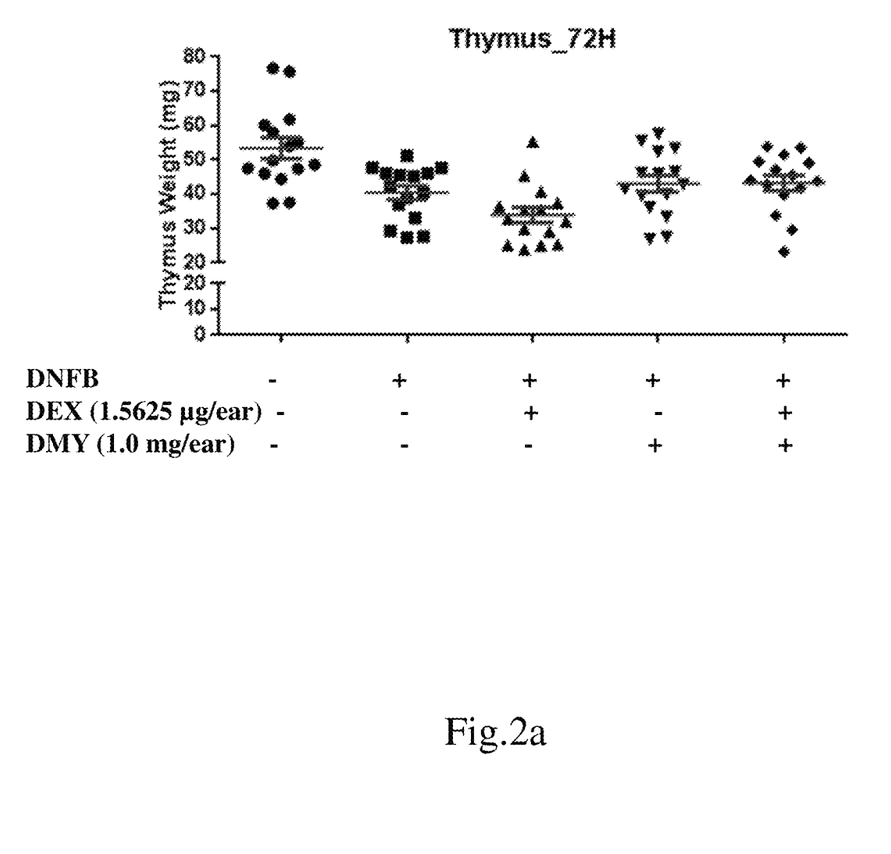
FIGS. 2a and b show the effect of different groups, including DEX, DMY and the formulation comprising DEX and DMY on thymus weight of DTH mice induced by DNFB.
Figure 2B:
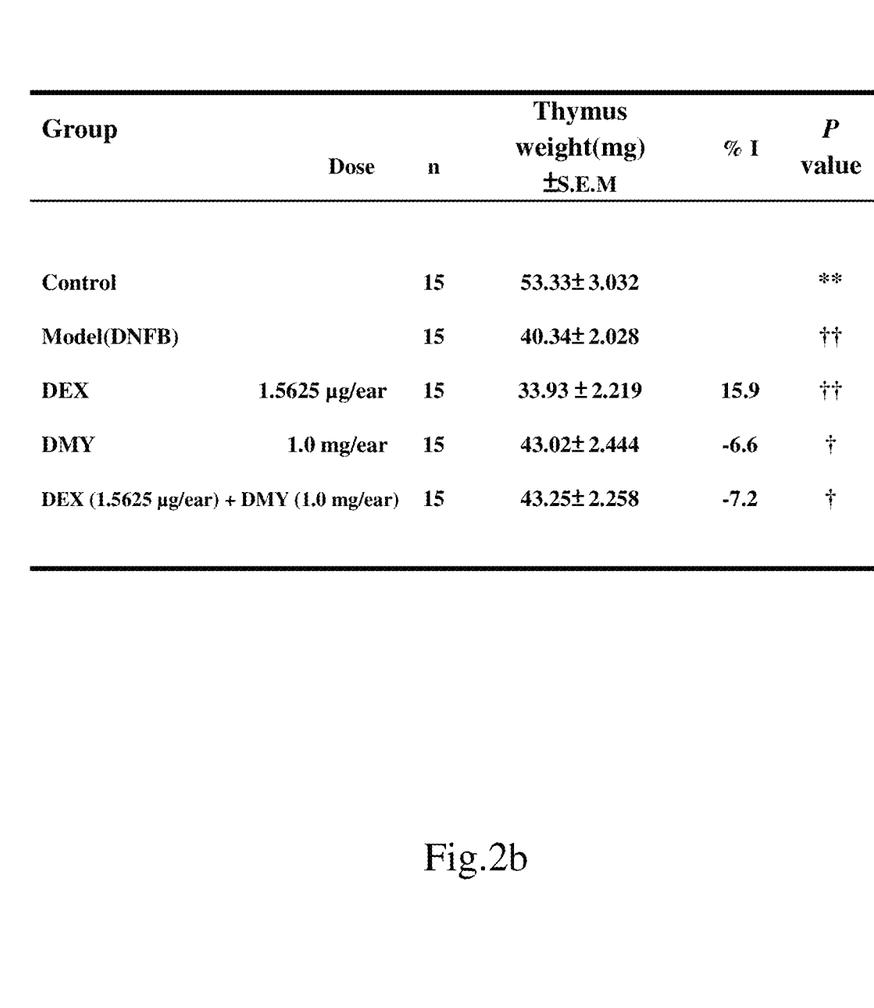

FIGS. 2a and 2b show that the effect of DEX, DMY and the combinational application of DMY and DEX (illustrated as the DMY+DEX group) on thymus weight of DTH mice induced by DNFB. Statistically significant differences with respect to the Model Group or Control Group are expressed as *$P<0.05$, **$P<0.01$; † $P<0.05$ and †† $P<0.01$ (Dunnett's t test), respectively. Percentages of inhibitory rate for each measurement were calculated from values for the DEX, DMY and DMY+DEX groups with respect to those for the Model Group. As shown in FIGS. 2a and b, in addition of DMY, the formulation could significantly prevent thymus atrophy induced by DEX.

In short, Example 2 shows the protective effect of DMY on thymus degeneration and the side effect of DEX, when it was used to treat ear edema induced by DNFB.

EXAMPLE 3

Study on the effect of DEX, DMY and the formulation comprising DEX and DMY on the population of CD4+ and CD8+T cell 3.1 Procedure—Flowcytometery Assay for Detection of CD4 and CD8 Expression The animal model was conducted as mentioned in section 1.1 of Example 1 above, in which after the mice were sacrificed by cervical dislocation, the thymocytes were isolated and washed by PBS. The cells were stained by 20 µL CD4 with CD8 for 30 min avoiding from light, followed by 4% PFA to fix the cells, and flow cytometery was then conducted.

3.2 Results

Figure 3:
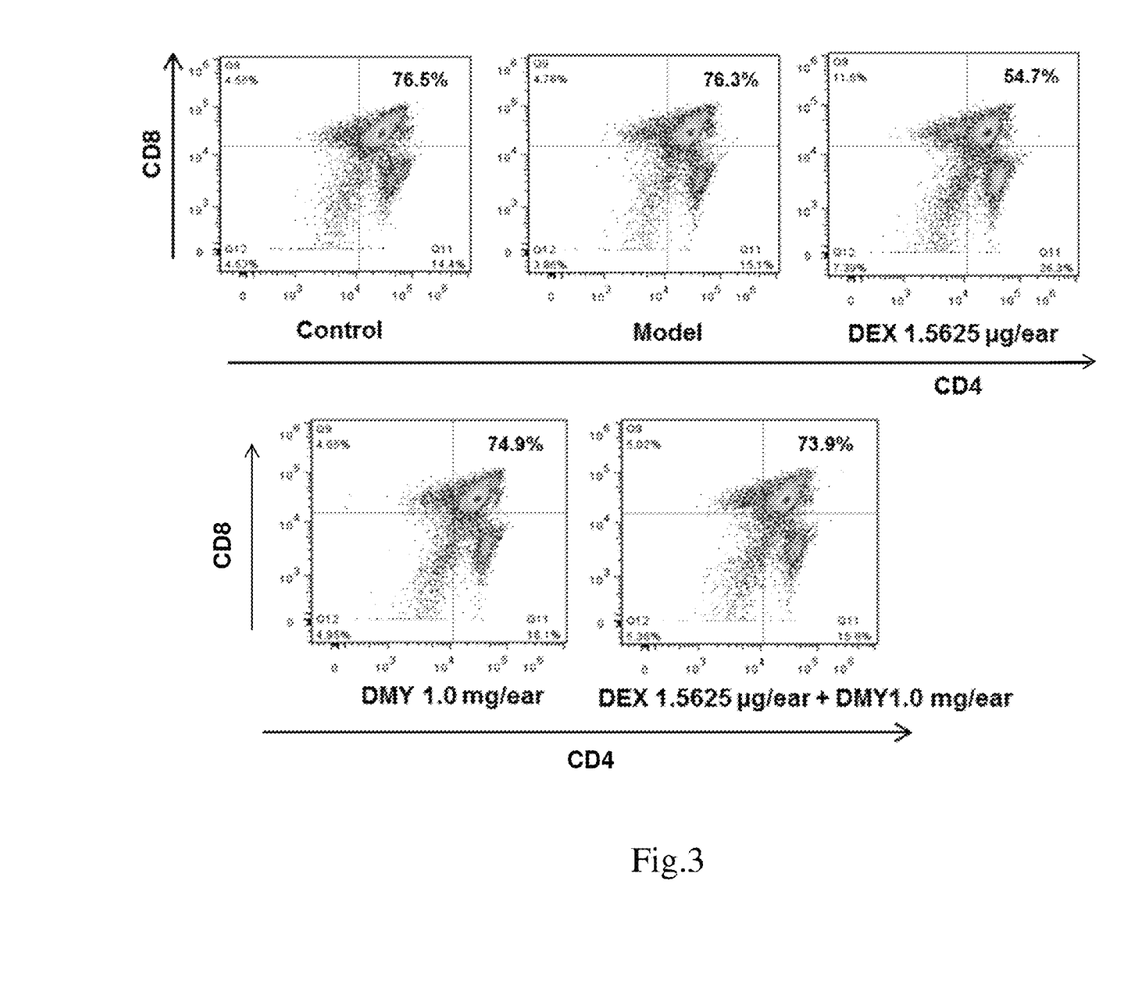
FIG. 3 shows the effect of different groups, including DEX, DMY and the formulation comprising DEX and DMY on the population of CD4+CD8+ thymocytes.

As illustrated in FIG. 3, the assay shows that CD4+CD8+ T cell is about 76% in the thymuses of the control and model groups. When the mice were topically applied by DEX, the CD4+CD8+ T cell population could be decreased to 54.7%. While in the addition of DMY, the ratio of CD4+CD8+ could be recovered.

In short, Example 3 describes the assay to show that the effect of DMY, DEX and the formulation comprising DEX and DMY on immature T population in thymus.

EXAMPLE 4

Study on the effect of DEX, DMY and the formulation comprising DEX and DMY on the apoptosis of thymocytes.

4.1 Procedure—Flowcytometery Assay for Detection of Thymocyte Apoptosis

The animal model was conducted as mentioned in section 1.1 of Example 1 above. Thymocytes were washed by cold PBS and binding buffer, resuspended in binding buffer including Annexin V-FITC, and then incubated at room temperature for 10 minutes. After adding the binding buffer containing PI, the cells were incubated on ice for another 15 minutes. The data was analyzed by flow cytometry within one hour.

4.2 Results

Figure 4:
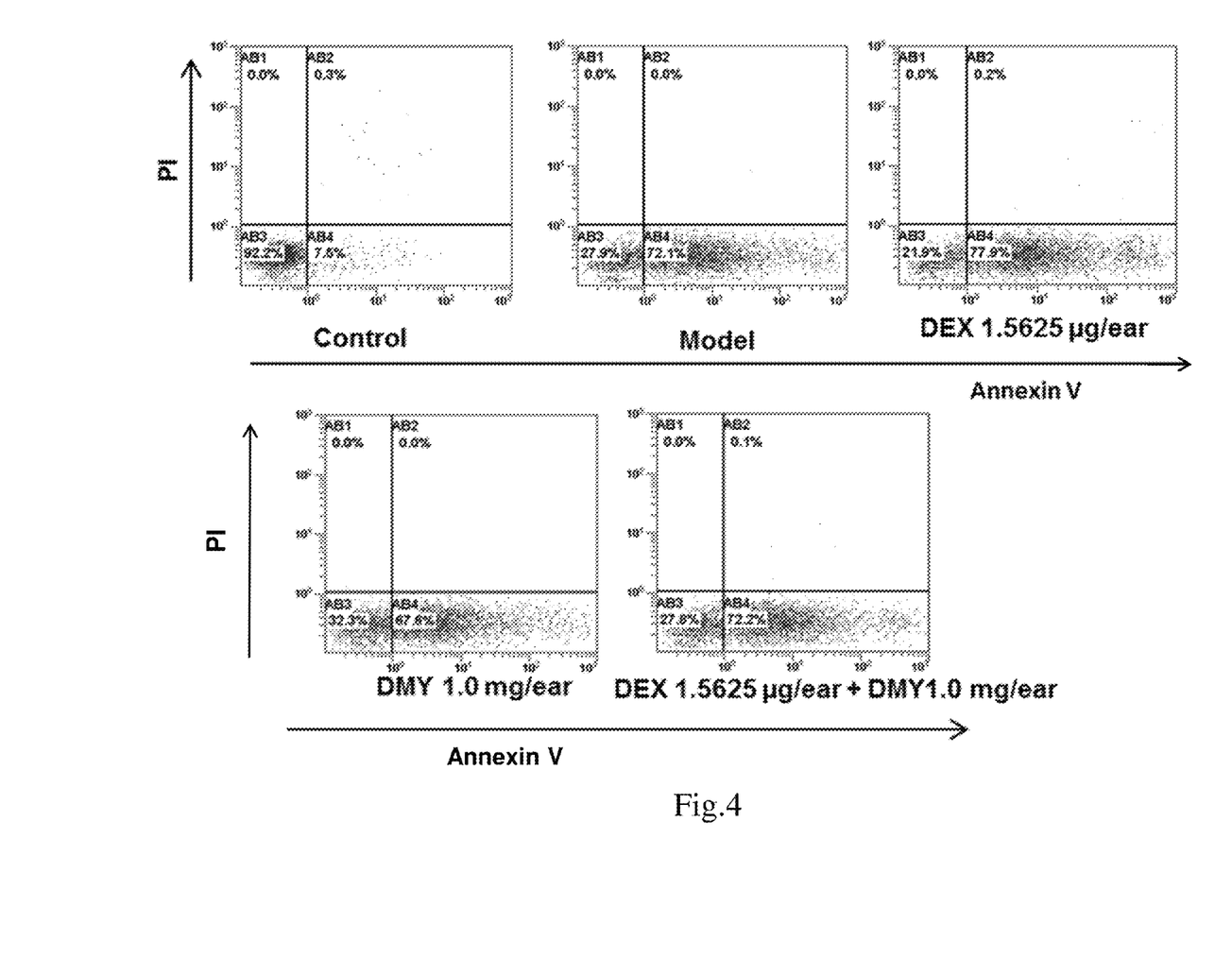
FIG. 4 shows the effect of different groups, including DEX, DMY and the formulation comprising DEX and DMY on the apoptosis of thymocytes.

As shown in FIG. 4, in the model group, the ratio of thymocyte apoptosis was about 72%, while DEX increased the ratio of apoptosis to 77.9%. In addition of DMY to DEX, the ratio of apoptotic cells was reduced to 72% in the formulation (DEX+DMY) group.

Example 4 shows the effect of DMY, DEX and the formulation comprising DEX and DMY on the apoptosis of thymocytes using Annexin V-FITC and PI.

EXAMPLE 5

Figure 5A:
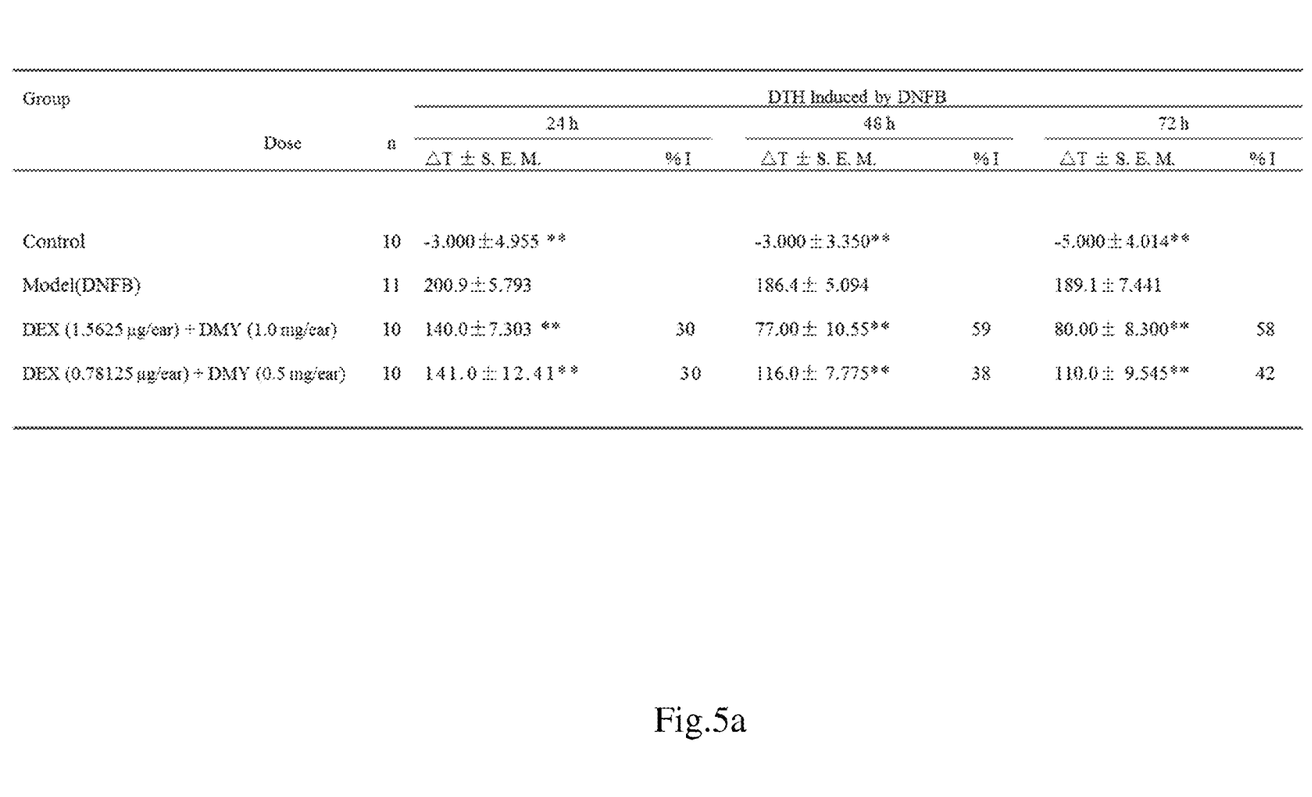
FIGS. 5a and b show that the formulation comprising DEX and DMY dose-dependently inhibits ear edema of Balb/c mice induced by DNFB.
Figure 5B:
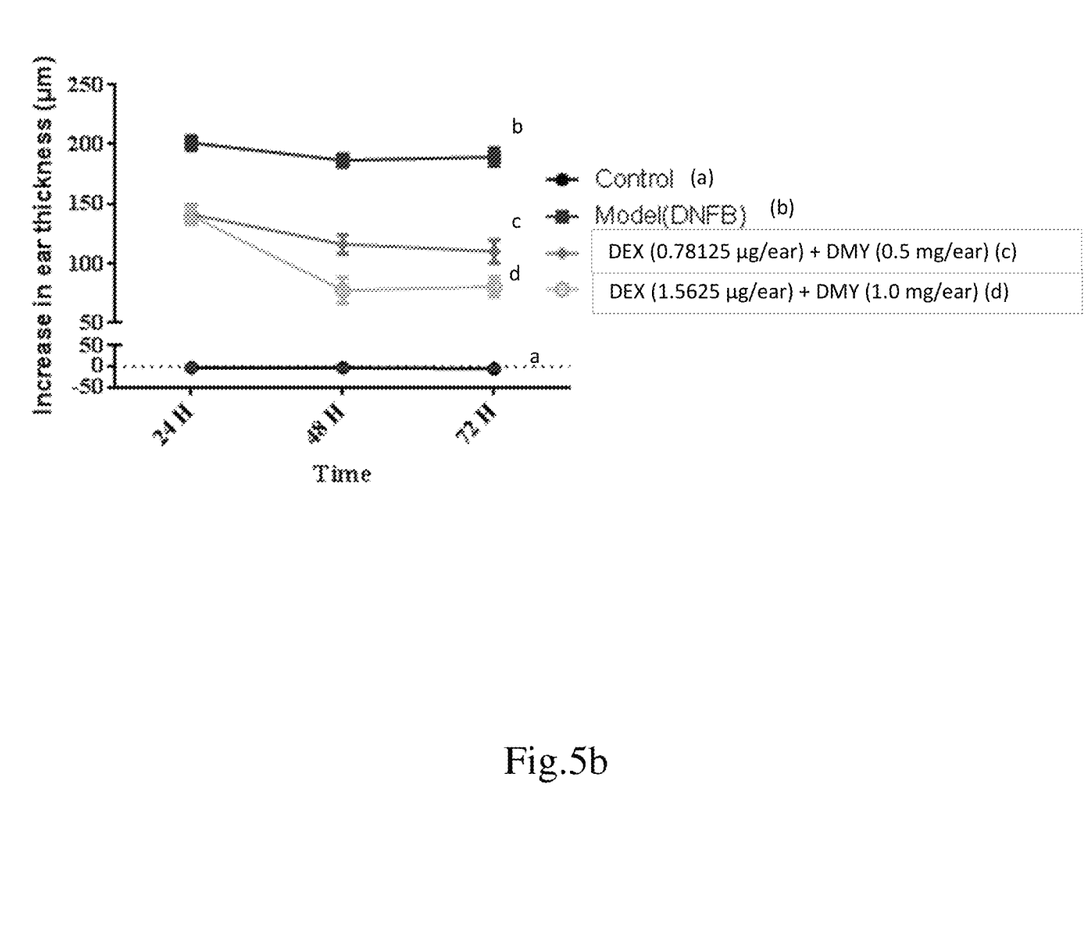

Study on the dose-dependent inhibitory effect and the formulation comprising DEX and DMY on ear edema of Balb/c mice induced by DNFB 5.1 Procedure and Results The animal model was conducted as mentioned in section 1.1 of Example 1 above. FIG. 5 shows the effect of the combinational application of DMY and DEX in a ratio of 640:1 (illustrated as the DMY+DEX group) on treatment of ear edema of DTH mice induced by DNFB. Edema as expressed as the increase in ear thickness (ΔT in micrometer±S.E.M.) in the DTH experiments. Percentages of inhibition (% I) for each measurement were calculated from values for the DMY+DEX group with respect to those for the Model. Statistically significant differences with respect to the Model Group are expressed as *$P<0.05$ and **$P<0.01$ (Dunnett's t test).

As illustrated in FIGS. 5a and 5b, the formulation comprising DMY and DEX in a ratio of 640:1 was dose-dependent and shown to significantly inhibit the ear edema induced by DNFB.

In short, Example 5 shows that the formulation comprising DMY and DEX could suppress the ear edema in a dose-dependent manner.

EXAMPLE 6

Study on the inhibitory effect of the formulation comprising DEX and DMY on thymus atrophy of Balb/c mice induced by DEX.

6.1 Procedure and Results

Figure 6A:
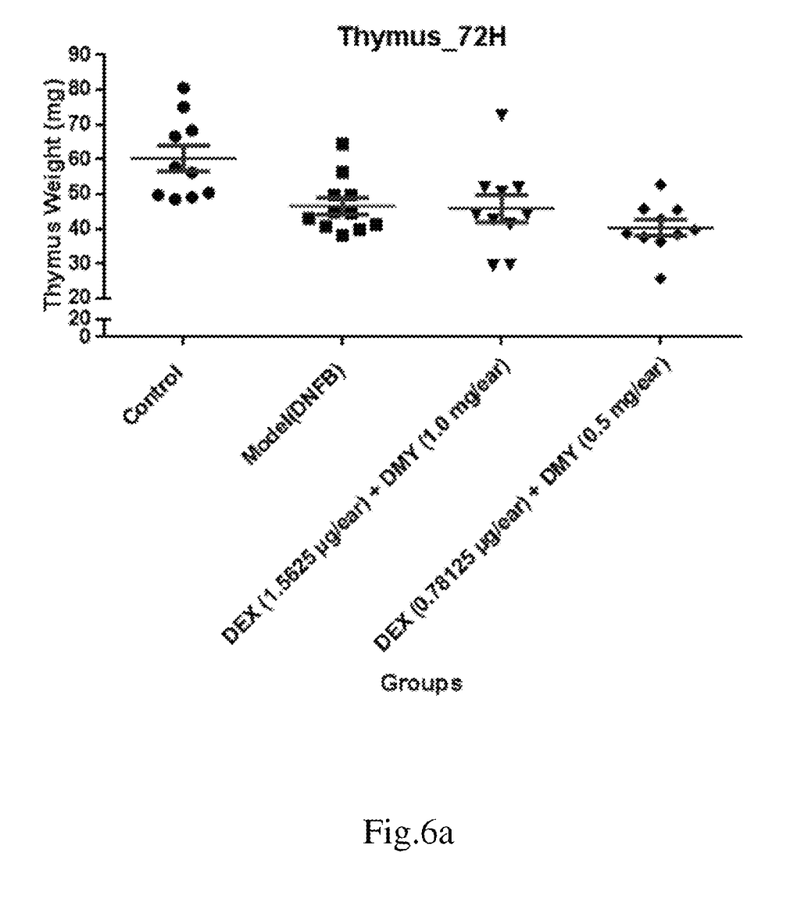
FIGS. 6a and b show that the formulation comprising DEX and DMY dose-dependently prevents thymus atrophy of Balb/c mice induced by DEX.
Figure 6B:
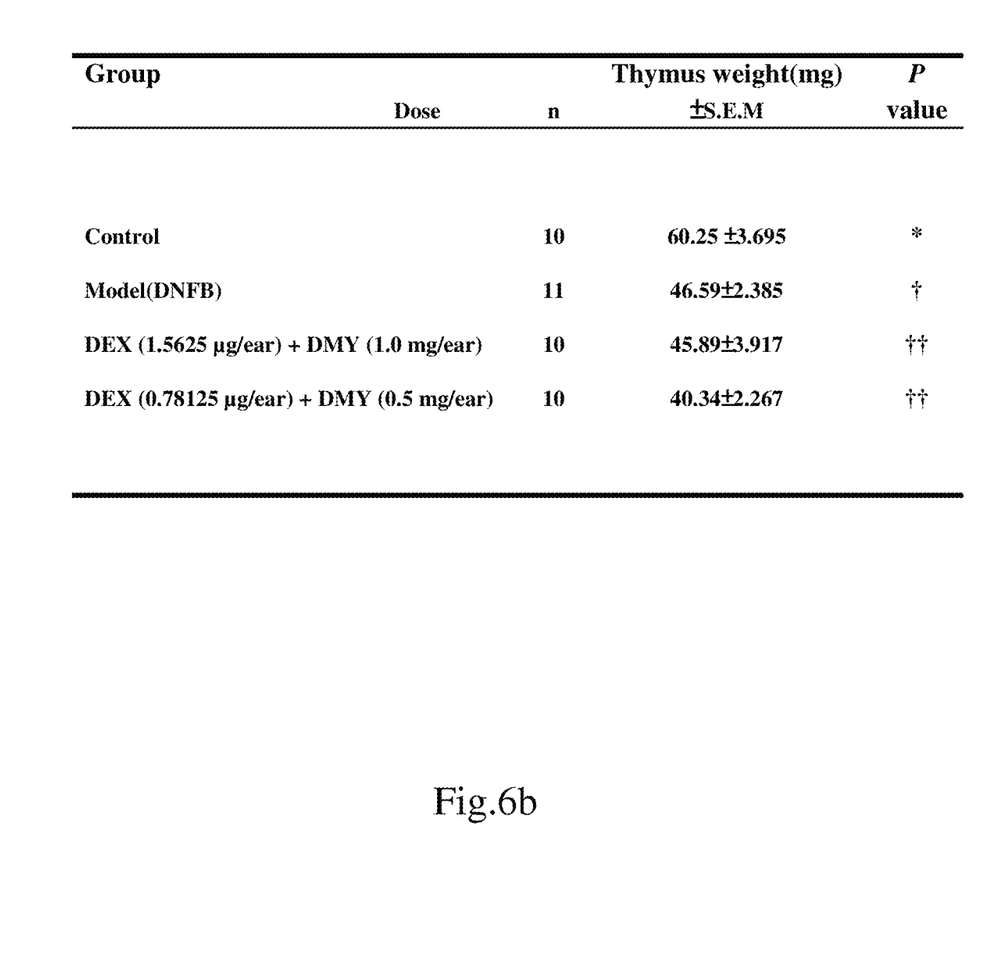

The animal model was conducted as mentioned method in section 1.1 of Example 1 above. FIG. 6 shows the effect of the combinational application of DMY and DEX (as illustrated in the DMY+DEX group) in a ratio of 640:1 after 72 hours of treatment on thymus weight of DTH mice induced by DNFB. Statistically significant differences with respect to the Model Group or Control Group are expressed as *$P<0.05$; † $P<0.05$ and †† $P<0.01$ (Dunnett's t test), where ns represents not significant.

As seen from FIGS. 6a and 6b, the formulation comprising DMY and DEX in a ratio of 640:1 was dose-dependent and shown to significantly prevent thymus atrophy.

In short, Example 6 shows that the formulation comprising DMY and DEX could prevent thymus atrophy induced by DEX in a dose-dependent fashion.

EXAMPLE 7

7.1 Study on the Immunohistochemical Staining Examination.

The animal model was conducted as mentioned in section 1.1 of Example 1 above. For CD4 and CD8 staining of ear sections, paraffin-embedded ears were sectioned and cut into 5-μm sections, hence then deparaffinized using xylene, 100% ETOH, 95% ETOH, 75% ETOH, and H2O series. Antigens were retrieved by steaming samples in DAKO target retrieval buffer (DAKO) for 20 minutes. After the nonspecific binding sites were blocked, the sections were incubated overnight at 4° C. with CD4 or CD8 antibodies (Phoenix Pharmaceuticals).

Sections were stained with 3,3'-diaminobenzidine substrate and counterstained with Meyer hematoxylin and eosin. Negative controls generated by the exclusion of the primary antibody and through the use of an unrelated isotype-matched IgG failed to demonstrate any specific labeling.

7.2 Study on Quantification of Signal-Joint TRECs

DNA was isolated from purified thymic T cells using DNA purification kit. PCR was performed using mδRec- and ψJα-specific primers and an mδRec-ψJα fluorescent probe as described previously. The standard curves for murine TRECs were generated using a mδRec-ψJα TREC PCR product cloned into a pc DNA3.1 plasmid from Prof. Gregory D. Sempowski (Duke Human Vaccine Institute, Duke University Medical Center, Durham, N.C., USA.). The assay was performed on slides according to previous study [1,2].

7.3 Results

Figure 7:
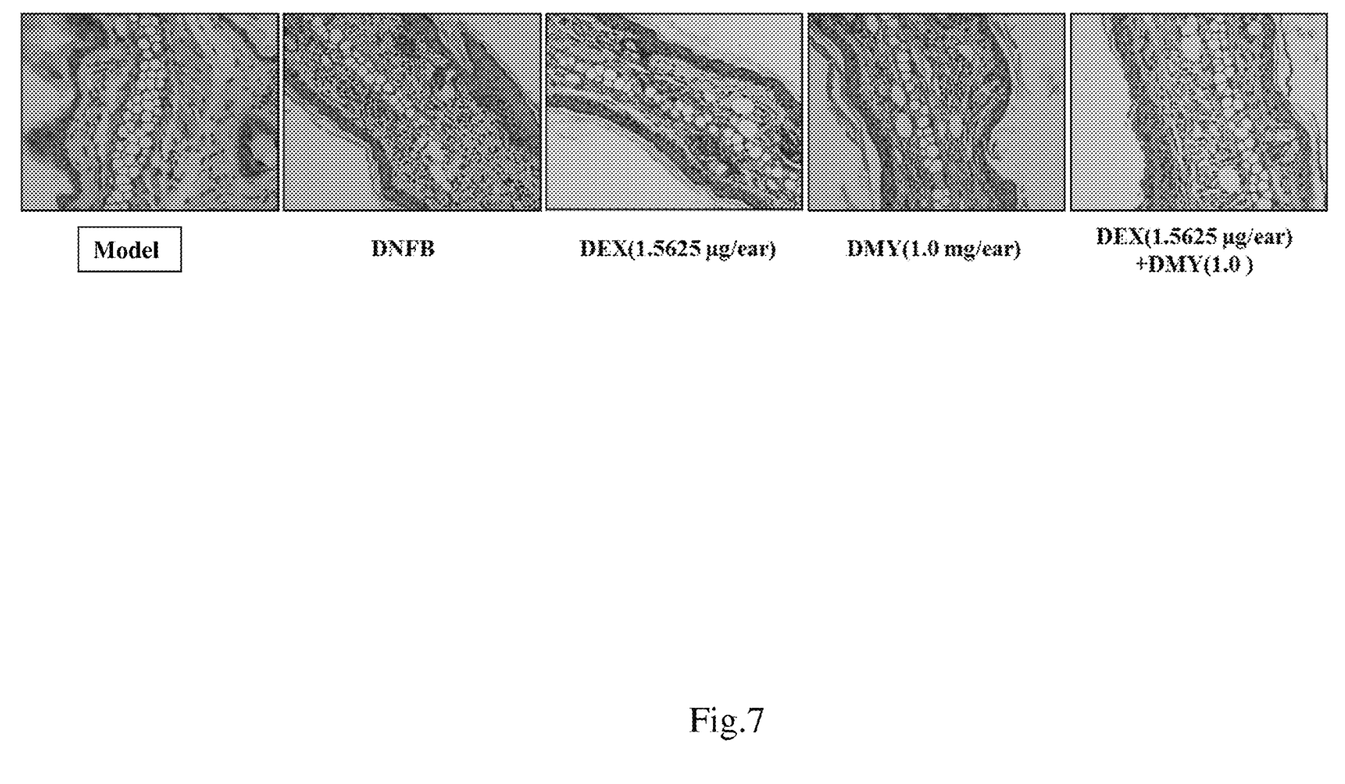
FIG. 7 shows that DMY, DEX and the formulation comprising DMY and DEX reduced DNFB-induced increase inflammation in ear. (Original magnification, ×100).
Figure 8:
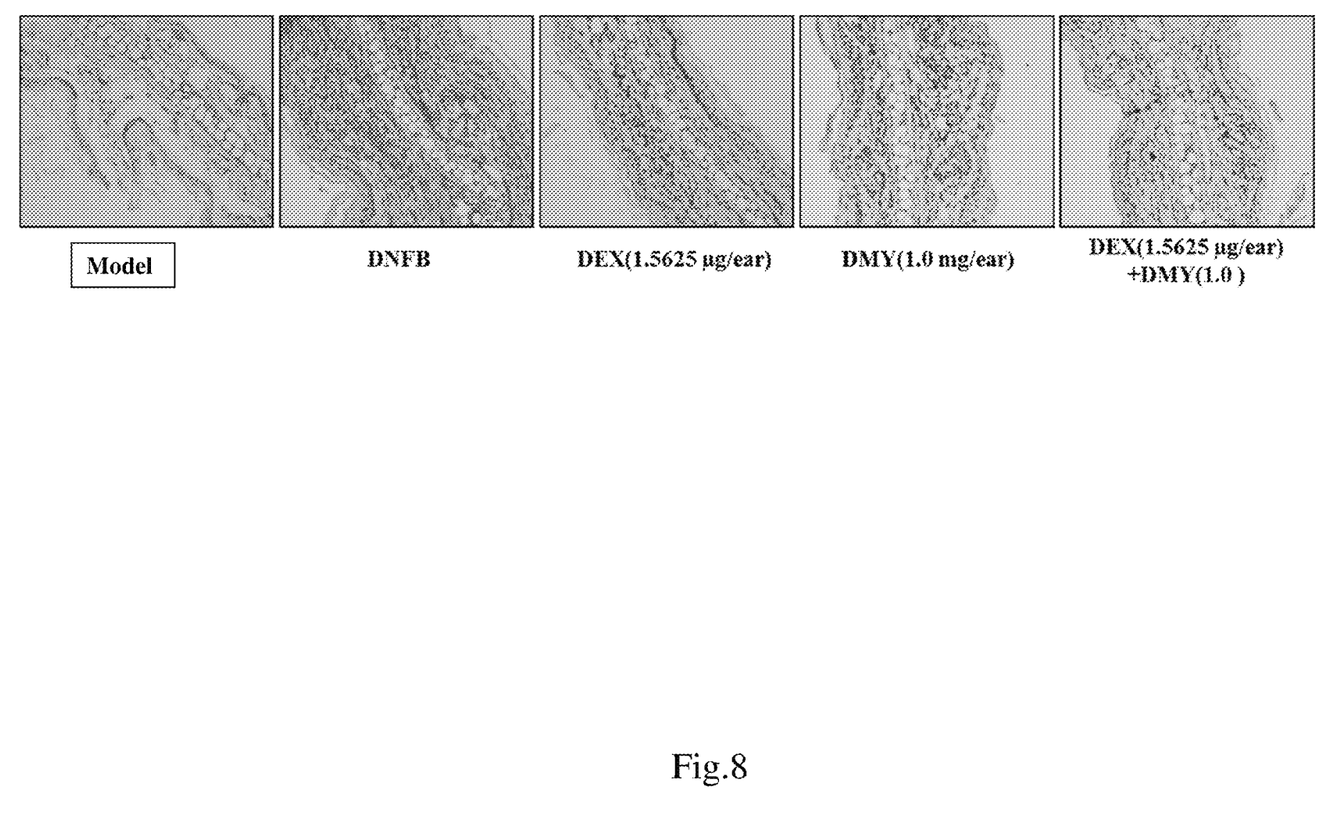
FIG. 8 shows that DMY, DEX and the formulation comprising DMY and DEX reduced DNFB-induced up-regulation of CD4+ T cell expression in ear. (Original magnification, ×100).
Figure 9:
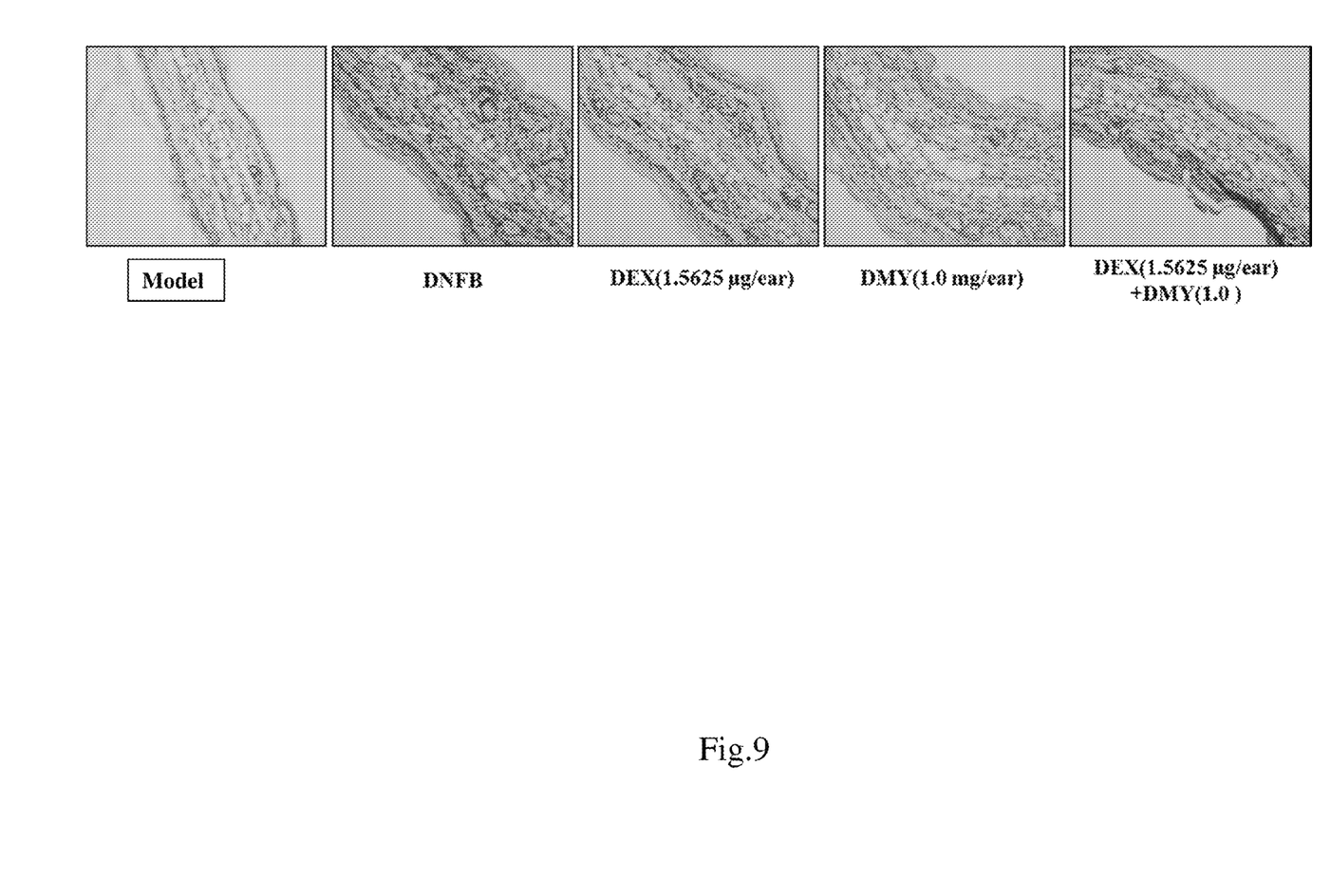
FIG. 9 shows that DMY, DEX and the formulation comprising DMY and DEX reduced DNFB-induced up-regulation of CD8+ T cell expression in ear. (Original magnification, ×100).

As shown in FIG. 7, DNFB treatment results in a marked increase of the prominent mononuclear cell infiltrate in the ear. When the mice were treated by DEX, DMY or the formulation comprising DEX and DMY, the number of inflammatory cells could be significantly reduced in the ear CD4+ and CD8+ lymphocytes are required as effector cells for DNFB-induced delayed-type hypersensitivity to develop fully [3], accounts of these cells in the ears punched from the mice were examined by immunohistochemical analysis. In FIGS. 8 and 9, the results showed that more inflammatory cells could be easily found in the DNFB-induced ears as compared to normal animals, while DEX, DMY and formulation comprising DEX and DMY (illustrated as the DMY+DEX group) were shown to reduce the accounts of CD4+ and CD8+ cells in the treated ears in comparison with the Model Group.

Figure 10:
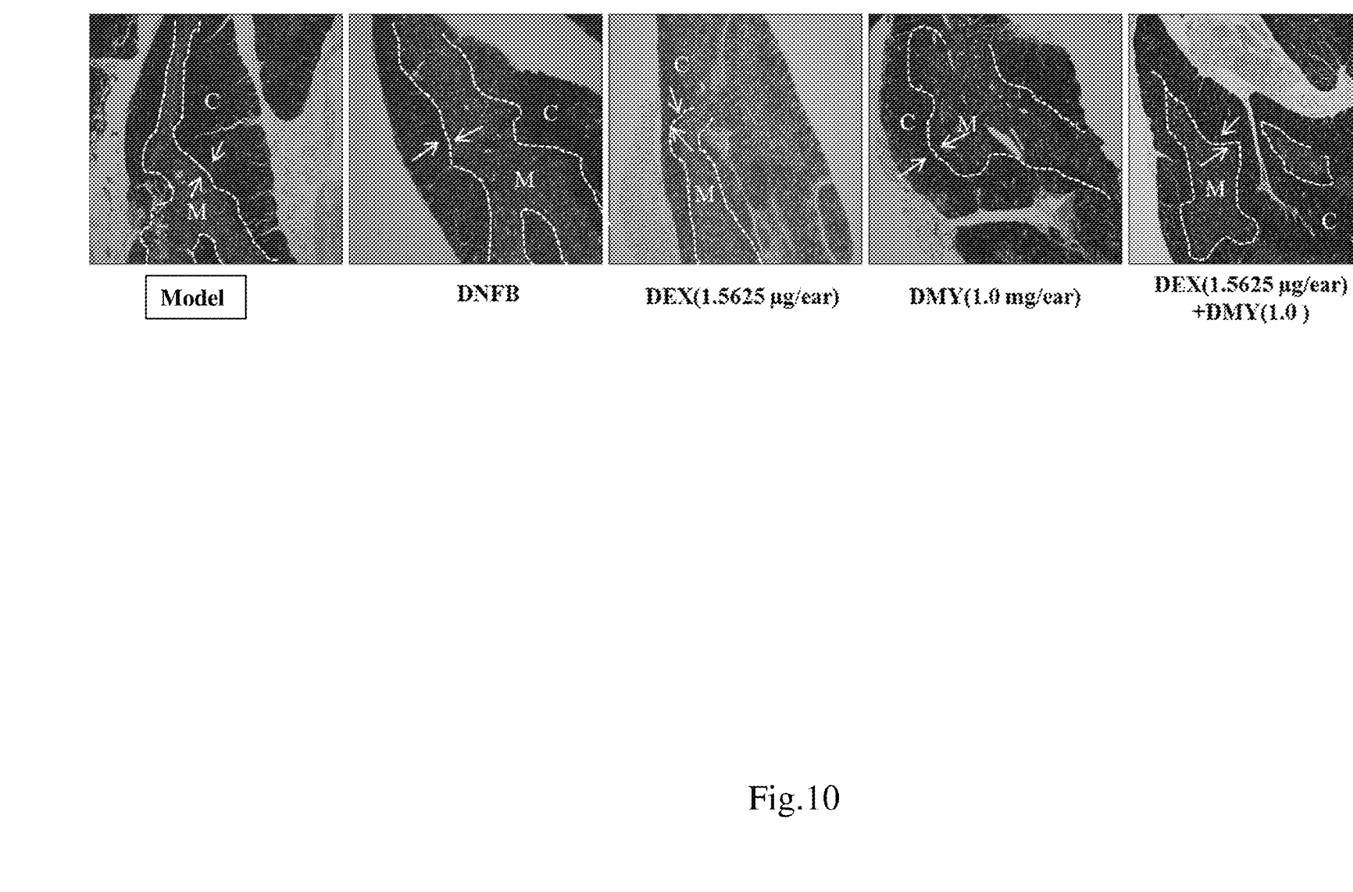
FIG. 10 shows that the formulation comprising DMY and DEX enhanced thymic cellularity compared to DEX-treated mice. (Original magnification, ×100).

On comparing with DEX-treated animals, DMY or the formulation comprising DMY and DEX was shown to significantly improve the thymic architecture according to the histological examination of thymus. As shown in FIG. 10, the groups of DMY or the formulation comprising DMY and DEX (illustrated as the DMY+DEX group) are associated with better defined corticomedullary junctions (dotted line) than DEX group, in which the site of junctions is the place where progenitors arrive in thymus.

Figure 11:
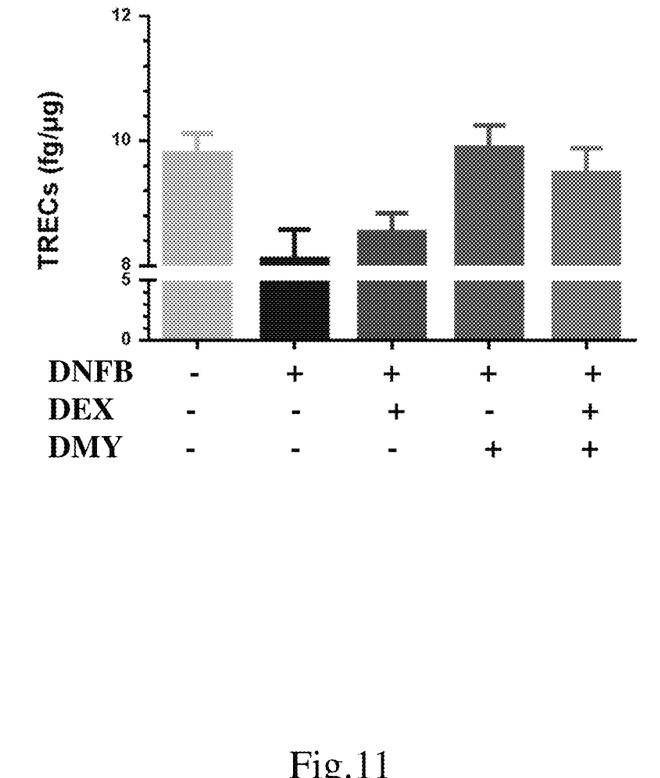
FIG. 11 shows that the formulation comprising DMY and DEX could improve the number of recent thymic emigrants compared to DEX-treated mice.

The T cell output and generation of the newly formed T cells from the thymus can be evaluated by quantifying the presence of TCR excision circles (TRECs) in thymus that have not proliferated after rearrangement of their TCR, as shown in FIG. 11. Given that formulation comprising DMY and DEX induces an increase in thymic weight and improvement of thymic architecture in the mice treated by DEX, thymopoiesis and recent thymic emigrants (RTEs) were quantified by measuring the excisional DNA of TCR gene rearrangement. On comparing with the DEX-treated animals, it was observed that DMY and the formulation comprising DMY and DEX could increase the levels of signal-joint TRECs in thymocytes, suggesting that DMY can protect or reverse the thymopoiesis in the DEX-treated animals.

In view of the above results, the formulation comprising DMY and DEX could enhance the anti-inflammatory effect of DEX on ear edema, and prevent the thymus atrophy mediated by DEX.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

REFERENCES

1. Sempowski, G. D., and Rhein, M. E. (2004) Measurement of mouse T cell receptor excision circles, Curr Protoc Immunol Chapter 10, Unit 10 31.
2. Lynch, H. E., and Sempowski, G. D. Molecular measurement of T cell receptor excision circles, Methods Mol Biol 979, 147-159.
3. Wang, B., Fujisawa, H., Zhuang, L., Freed, I., Howell, B. G., Shahid, S., Shivji, G. M., Mak, T. W., and Sauder, D. N. (2000) CD4+ Th1 and CD8+ type 1 cytotoxic T cells both play a crucial role in the full development of contact hypersensitivity, J Immunol 165, 6783-6790.

What is claimed is:

1. A method of treating thymus degeneration comprising administering an effective amount of dihydromyricetin to a subject in need thereof.

2. The method of claim 1, wherein said thymus degeneration is induced by dexamethasone.

3. The method of claim 1, wherein said thymus degeneration is induced by dexamethasone when said dexamethasone is used to treat inflammation.

4. The method of claim 3, wherein said dexamethasone exhibits a synergistic effect with said dihydromyricetin when said dihydromyricetin is used to treat inflammation.

5. The method of claim 4, wherein said dexamethasone and said dihydromyricetin have a dosage ratio in a range of 1 to 640.

6. A method of treating inflammation comprising administering an effective amount of dexamethasone and dihydromyricetin to a subject in need thereof, wherein said dexamethasone exhibits a synergistic effect with said dihydromyricetin in treating inflammation.

7. The method of claim 6, wherein said synergistic effect reduces thymus degeneration; wherein said thymus degeneration is induced during the treatment of inflammation.

8. The method of claim 7, wherein said thymus degeneration is induced by dexamethasone.

9. The method of claim 6, wherein said dexamethasone and said dihydromyricetin have a dosage ratio in a range of 1 to 640.

10. A formulation comprising an effective amount of dexamethasone and dihydromyricetin for treating inflammation, wherein said formulation can treat thymus degeneration induced during said treatment.

11. The formulation of claim 10, wherein the weight ratio of dexamethasone and dihydromyricetin is 1 to 640.

* * * * *